(12) United States Patent
Olson

(10) Patent No.: US 9,283,331 B2
(45) Date of Patent: Mar. 15, 2016

(54) HYPODERMIC NEEDLE SYSTEM AND METHOD OF USE TO REDUCE INFECTION

(75) Inventor: Randall J. Olson, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 1204 days.

(21) Appl. No.: 13/176,625

(22) Filed: Jul. 5, 2011

(65) Prior Publication Data

US 2012/0136337 A1 May 31, 2012

Related U.S. Application Data

(60) Provisional application No. 61/418,337, filed on Nov. 30, 2010.

(51) Int. Cl.
*A61M 5/32* (2006.01)
*A61F 9/00* (2006.01)
*A61M 5/34* (2006.01)

(52) U.S. Cl.
CPC .............. *A61M 5/329* (2013.01); *A61F 9/0008* (2013.01); *A61M 2005/341* (2013.01); *A61M 2205/0205* (2013.01); *A61M 2210/0612* (2013.01)

(58) Field of Classification Search
CPC ..................... A61M 2005/3226; A61M 39/14; A61M 25/0643; A61M 2005/3228; A61M 5/3243; A61M 2005/3212; A61M 5/321; A61M 25/0097; A61M 25/10; A61M 39/162; A61M 39/20; A61M 39/0247; A61M 39/16; A61M 39/0208; A61M 2039/1072; A61M 2039/0063; A61M 2039/0258; A61M 2039/0261; A61M 2039/0273; A61M 2039/0279; A61M 2025/0019; A61M 2025/0056; A61M 2005/1588; A61M 1/285; A61M 16/0463; A61M 2005/312; A61M 2005/341; A61M 2205/0205; A61M 2210/0612; A61M 25/0041; A61M 5/3134; A61M 5/346; A61F 9/0008; A61K 9/0019

USPC ........ 604/272, 168.01, 198, 122, 170.01, 415
See application file for complete search history.

(56) References Cited

U.S. PATENT DOCUMENTS 4,552,561 A * 11/1985 Eckenhoff et al. ......... 604/891.1
5,312,345 A     5/1994 Cole (Continued)

FOREIGN PATENT DOCUMENTS

CN     1085107 A    4/1994
CN     2882643 Y    3/2007

(Continued)

OTHER PUBLICATIONS

International Preliminary Report on Patentability from related PCT-US2011/050061, dated Apr. 13, 2013.
International Search Report from related PCT Patent Application No. PCT/US2011/050061, Apr. 13, 2012.
English Translation of Office Action from Chinese Application No. 201180057485.2, dated Oct. 10, 2014.

*Primary Examiner* — Bhisma Mehta
*Assistant Examiner* — Brandy S Lee
(74) *Attorney, Agent, or Firm* — Snow Christensen & Martineau; Randall B. Bateman

(57) ABSTRACT

A hypodermic needle system and method for reducing the incidence of infections due to administering fluids by injection to humans or animals is provided. The hypodermic needle system may include a needle with an insert disposed within its hollow channel to substantially prevent bacteria, fungi and/or other organisms/contaminants, which may be present on the exterior surface to be penetrated, from adhering to the inner surfaces of the needle's channel or become trapped in the needle bore. The hypodermic needle system may include a film that covers at least one surface of the needle or insert, and/or have a bent or curved tip to reduce the ability of infectious agents to adhere to said surface/space within the needle. Additionally, the hypodermic needle system may include an anti-infection agent, such as an antibiotic or antiseptic to further reduce the incidence of infections, and may include an attachment member which reduces the risk of infection.

25 Claims, 10 Drawing Sheets

(56) References Cited

U.S. PATENT DOCUMENTS

| | | | |
|---|---|---|---|
| 5,669,882 A * | 9/1997 | Pyles | 604/170.03 |
| 6,254,574 B1 | 7/2001 | Burzynski et al. | |
| 6,391,007 B2 | 5/2002 | Chang et al. | |
| 6,544,239 B2 | 4/2003 | Kinsey et al. | |
| 6,761,704 B2 | 7/2004 | Crawford | |
| 6,837,878 B2 | 1/2005 | Smutney et al. | |
| 6,936,053 B1 * | 8/2005 | Weiss | 606/107 |
| 7,001,361 B2 | 2/2006 | Polidoro | |
| 2005/0124941 A1 * | 6/2005 | Panchula et al. | 604/218 |
| 2005/0261632 A1 | 11/2005 | Xu | |
| 2007/0299409 A1 | 12/2007 | Whitbourne et al. | |

FOREIGN PATENT DOCUMENTS

| | | | |
|---|---|---|---|
| GB | 624269 | 6/1949 | |
| JP | 10-328302 | 12/1998 | |
| JP | 2006006465 * | 6/2004 | A61B 1/00 |
| JP | 2006-006465 | 1/2006 | |
| JP | 2006-006465 A | 1/2006 | |

* cited by examiner

HYPODERMIC NEEDLE SYSTEM AND METHOD OF USE TO REDUCE INFECTION

RELATED APPLICATIONS

The present application claims the benefit of U.S. Provisional Application Ser. No. 61/418,337, filed Nov. 30, 2010, which is herein incorporated by reference in its entirety.

BACKGROUND OF THE INVENTION

1. The Field of the Invention

The present invention relates to a hypodermic needle system and a method to reduce the incidence of infections caused when injecting fluids into a human or animal. More particularly, the present invention relates to a hypodermic needle with a removable insert disposed in the hollow channel of the needle which may protect the channel from becoming contaminated prior to delivery of a pharmaceutical compound or other therapeutic agent to a patient.

2. State of the Art

There are many methods for administering a compound to achieve a therapeutic effect in humans or animals known in the art, such as ingestion, inhalation, injection, and transmucosal administration. There are, however, advantages and disadvantages with each of these methods of administration. For example, ingestion may be the simplest way to administer a pharmaceutical compound or other therapeutic agent, e.g. a drug, and may be preferred by patients over other methods, but a drug that is ingested will be subjected to the low pH of the gastric juices and the first-pass effect of the liver. Thus, drugs that are ingested are often administered at relatively high doses which can cause unwanted side effects. Additionally, the site of action for a drug can limit whether they can be administered orally, such as when a biological barrier would have to be crossed.

The disadvantages of administering a drug through ingestion can be overcome by injecting the drug directly at its site of action, but administering the drug by injection increases the chance of infection in the patient. Although infection due to injections can often be minimized by using proper aseptic technique, there are a variety of procedures in which a needle must be inserted into the body through a tissue which cannot be readily sterilized. However, because other methods of administering the drug may be less effective or not effective at all, it may be required to inject the drug anyway to effectively treat a particular disease or condition. This is often the case, for example, when treating eye diseases or conditions because the blood-ocular barrier keeps most drugs out of the eye.

Under normal circumstances, the blood-ocular barrier protects a human or animal by providing natural resistance against organisms invading the vitreous humor, the clear gel that fills the space between the lens and the retina of the eyeball. The immune response of a human or animal to an organism that is introduced into the vitreous humor is more limited than if the organism was present in other areas of the body. Thus, a medical procedure that disrupts the integrity of the globe of the eye, such as intravitreal injections to treat a disease or condition of the eye, can lead to infection and inflammation of the eye, i.e. endophthalmitis. It has been found that when the needle passes through the exterior membranes surrounding the eyeball (the conjunctiva), bacteria, which are present normally, can be introduced into the interior hollow channel of the needle and ultimately deposited in the vitreous humor when a substance is injected.

Moreover, because the conjunctiva cannot be readily sterilized prior to intravitreal injections the risk of infection is not as minimal as is desired with such injections. Some, common complications of endophthalmitis are decreased vision and/or permanent vision loss. Some patients may even require enucleation to eradicate a blind and painful eye.

Intravitreal injection of various drugs has become a mainstay of treatment in ophthalmology. It is currently estimated that approximately 1000 to 3000 infections due to intravitreal injection occur each year with approximately half of those infections resulting in legal blindness. The number of injections given each year is increasing as the understanding of how to treat certain eye diseases or conditions increases, and/or new drugs for treating such diseases or conditions become available. For example intravitreal injections may be given to treat viral retinitis, age-related macular degeneration, cystoid macular edema, diabetic retinopathy, uveitis, vascular occlusions, and even endophthalmitis.

Thus, there is a need for a hypodermic needle system and method that substantially minimizes infections caused by injections of fluids in humans and animals. It is desirable that such a hypodermic needle system is relatively easy to use. It is also desirable to provide such a hypodermic needle system which is inexpensive and easy to manufacture.

SUMMARY OF THE INVENTION

It is an object of the present invention to provide a hypodermic needle system and method of use to reduce the incidents of infection.

According to one aspect of the present invention, a hypodermic needle system may include a needle and an insert disposed within the hollow channel of the needle and configured to substantially obstruct the channel at the penetrating end of the needle.

According to another aspect of the present invention, the insert of the hypodermic needle system may substantially prevent bacteria, fungi, or other organisms/contaminates from entering the hollow channel of the needle.

According to another aspect of the present invention, the insert of the hypodermic needle system may be beveled.

According to still another aspect of the present invention, the insert of the hypodermic needle system may be disposed in alignment with the beveled end of the hypodermic needle.

According to yet another aspect of the present invention, the insert of the hypodermic needle system may be removable.

According to another aspect of the present invention, the hypodermic needle system may include a needle with a bent tip. The tip of the needle may be bent at the bevel so that penetration can be made with a linear puncture.

In accordance with another aspect of the present invention, a hypodermic needle system is provided comprising a needle having a beveled end and an insert having a beveled face, wherein the beveled end of the needle and the beveled face of the insert are positioned relative to each other so as to form a substantially single, planar surface.

According to still another aspect of the present invention, a hypodermic needle system may include a film covering a surface of the penetrating end of the hypodermic needle system. The film may reduce adherence of bacteria, fungi, or other organisms/contaminates to the surfaces of the hypodermic needle system.

In accordance with one aspect of the present invention, the film of the hypodermic needle system may be a thermoplastic such as poly methyl methacrylate ("PMMA") or other substance that resists adherence of bacteria, fungi, or other organisms/contaminates to the surfaces of the hypodermic needle system and substantially eliminates any space where microorganisms may be trapped.

According to another aspect of the invention, the hypodermic needle system may comprise an antibiotic, antifungal, or sterilizing compound.

According to another aspect of the invention, a hypodermic needle system may include a needle attached to a medicament container, such as a syringe, wherein the needle may comprise a removable insert disposed within the hollow channel of the needle, and wherein the insert may be removed from the hollow channel of the needle while the needle is attached to the medicament container.

In accordance with one aspect of the present invention, a method of reducing the incidence of infections due to administering fluids by injection to humans or animal may be provided that may comprise disposing an insert within the hollow channel of a needle prior to penetrating an exterior surface of the human's or animal's body so as to substantially reduce the amount of bacteria, fungi and/or other organisms/contaminants that may be transmitted from an external surface to any internal area of the human's or animal's body, then removing the insert after the needle has penetrated the external surface to administer the fluid.

These and other aspects of the present invention are realized in a hypodermic needle system and method of use as shown and described in the following figures and related description.

BRIEF DESCRIPTION OF THE DRAWINGS

Various embodiments of the present invention are shown and described in reference to the numbered drawings wherein.

Figure 1:
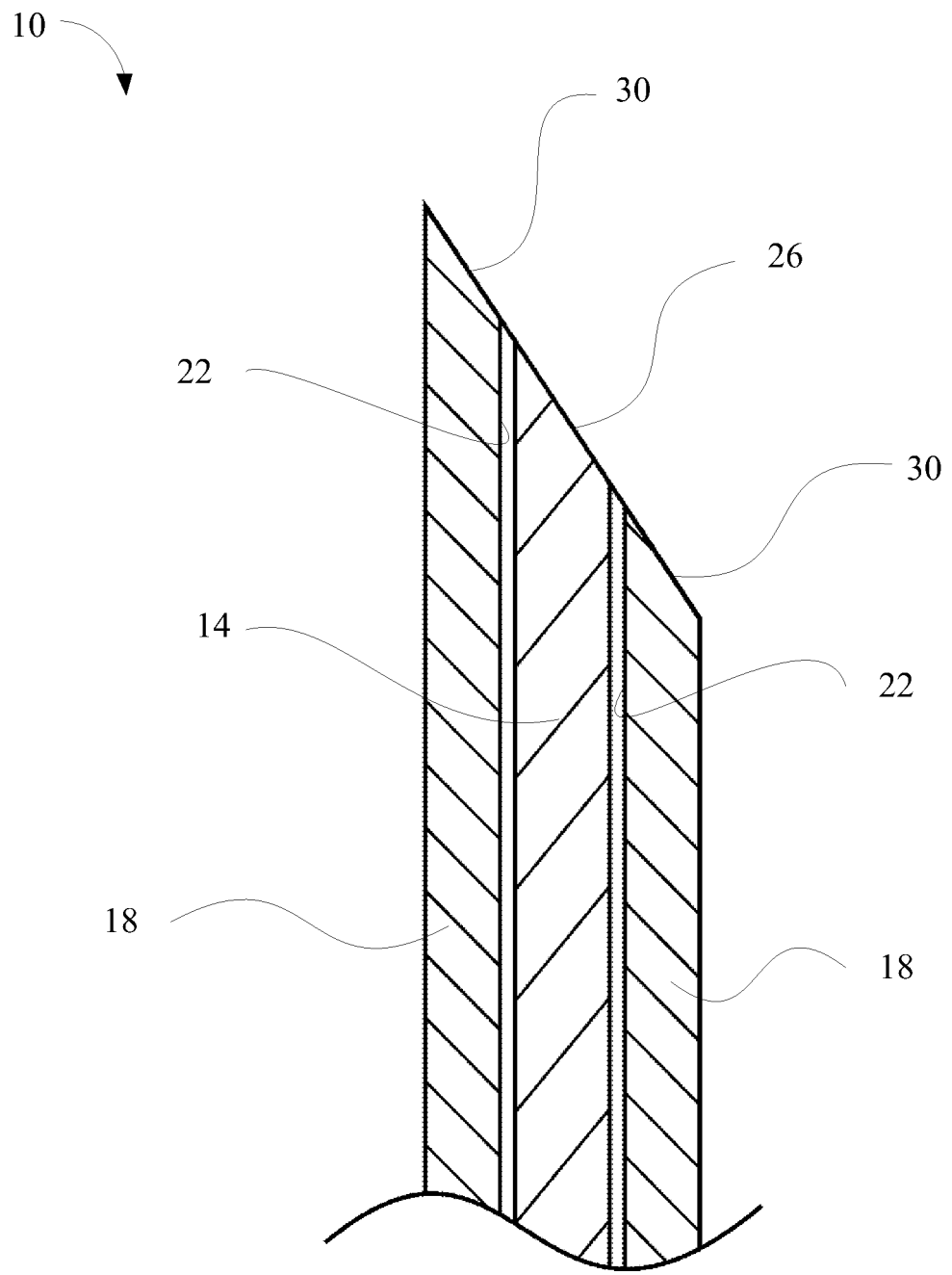
FIG. 1 shows a fragmented, cross-sectional side view of a hypodermic needle system made in accordance with the principles of the present invention.

It will be appreciated that the drawings are illustrative and not limiting of the scope of the invention which is defined by the appended claims. The various elements of the invention accomplish various aspects and objects of the invention. It is appreciated that not every element of the invention can be clearly displayed in a single drawing, and as such not every drawing shows each element of the invention.

DETAILED DESCRIPTION

The drawings will now be discussed in reference to the numerals provided therein so as to enable one skilled in the art to practice the present invention. The drawings and descriptions are exemplary of various aspects of the invention and are not intended to narrow the scope of the appended claims. It will be appreciated that the various aspects of the hypodermic needle systems discussed herein may be the same. Different reference numerals may be used to describe similar structures in the various hypodermic needle systems for clarity purposes only.

Turning to FIG. 1, there is shown a fragmented, cross-sectional view of a hypodermic needle system, generally indicated at 10, according to principles of the present invention. The hypodermic needle system 10 may include an insert 14 disposed within the hollow channel of a needle 18 so as to substantially prevent bacteria, fungi, or other organisms/contaminates from entering the channel and attaching to the inner sidewalls 22 of the needle 18. The insert 14 may be comprised of wire, plastic or other suitable materials.

When administering a pharmaceutical compound or other therapeutic agent to a human or animal by injection, the tissue surface that is to be penetrated by the needle 18 is typically sterilized with a chemical, usually alcohol, however, this is more difficult with a mucous membrane like conjunctiva that covers the eye. If the tissue surface is not sterilized then the risk of causing an infection significantly increases because it is normal for a vast number of bacteria and other contaminants to occupy the exterior tissue surfaces of humans and animals, e.g. the human's or animal's normal flora. Thus, if the exterior tissue surface is not sterilized the bacteria and other contaminants will adhere to the surfaces of the needle 18 and be transferred to an inner area of the human or animal where they may cause an infection.

In some instances, the bacteria or other contaminants that are more likely to cause infection are those that adhere to the inner surface 22 of the needle 18. Several factors may contribute to such a phenomenon. For example, bacteria that adhere to the outer surface of needle 18 may be mechanically removed as the needle 18 passes through the exterior tissue surface, i.e. are wiped off. Also, bacteria that adhere to the inner surface 22 may be washed off by the flow of fluid through the hollow channel of needle 18 once the fluid is injected inside the human or animal. Therefore, the incidence of infections due to procedures requiring an injection may be reduced by using the hypodermic needle system 10 which includes insert 14 because insert 14 will substantially prevent or reduce bacteria, fungi, and/or other contaminants adhering to the inner surface 22 of needle 18, and such contaminates will be mechanically removed from the face 26 as the needle 18 passes through an exterior tissue surface.

Use of the hypodermic needle system 10 may be particularly beneficial when the needle 18 must be inserted into the body through a tissue which cannot be readily sterilized.

However, those skilled in the art will appreciate that use of hypodermic needle system 10 may reduce the number of infections even when the tissue could be easily sterilized using a chemical agent because the practice of aseptic technique often varies greatly among medical personnel.

As can also be seen in FIG. 1, insert 14 of hypodermic needle system 10 may comprise a beveled face 26 that is disposed substantially in alignment with the beveled edge 30 of a typical needle 18. The edge 30 of needle 18 is beveled to create a sharp pointed tip letting the needle 18 easily penetrate the tissue surface. Thus, by providing an insert 14 with a beveled face 26 that is substantially aligned with the beveled edge 30 of needle 18, the insert 14 does not interfere with penetration when substantially all of inner surface 22 is protected.

Figures 2A, 2B:
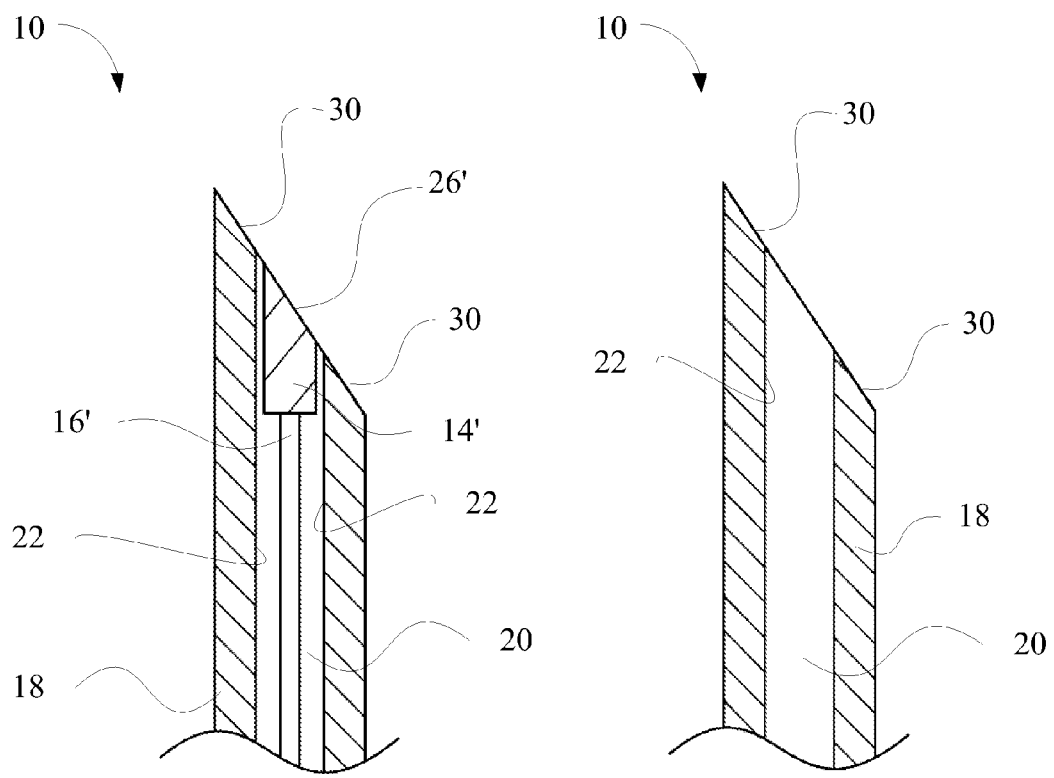
FIG. 2A shows a fragmented cross-sectional view of a hypodermic needle system according to principles of the present invention with an alternate insert disposed within the hollow channel of a needle.
FIG. 2B shows a fragmented, cross-sectional side view of a hypodermic needle system with the insert removed.

Now turning to FIG. 2A, there is shown a fragmented cross-sectional view of a hypodermic needle system, generally indicated at 10, with an alternate insert 14' disposed within the hollow channel 20 of a needle 18. Insert 14' is disposed within the hollow channel 20 adjacent the penetrating end of hypodermic needle 18 so as to substantially prevent bacteria, fungi, and/or other contaminants from contacting inner surface 22 of needle 18. Similar to insert 14 of FIG. 1, insert 14' may comprise a beveled face that is substantially aligned with beveled edge 30. Insert 14', however, may comprise a line 16' that may be attached to insert 14'. One of ordinary skill in the art will appreciate that line 16' may comprise wire, string, cord, etc.

FIG. 2B shows a fragmented, cross-sectional side view a hypodermic needle system 10 without the insert (reference numerals 14 and 14' in FIGS. 1 and 2 respectively). Line 16' (FIG. 2A) may be used for removing the insert 14' once the needle 18 has penetrated an exterior tissue surface. Alternatively, the insert 14 (FIG. 1) itself may be used for removing the insert from the hollow channel 20 of needle 18 after it has penetrated an exterior tissue surface.

The insert 14' may be removed by pulling string 16' in the direction away from the penetrating end of the hypodermic needle system 10. Once the insert 14' is removed, a fluid, such as a pharmaceutical compound or other therapeutic agent, may be administered to a human via hollow channel 20 with fewer or no infectious agents being washed off of inner surface 22 into the human or animal patient.

Figure 3:
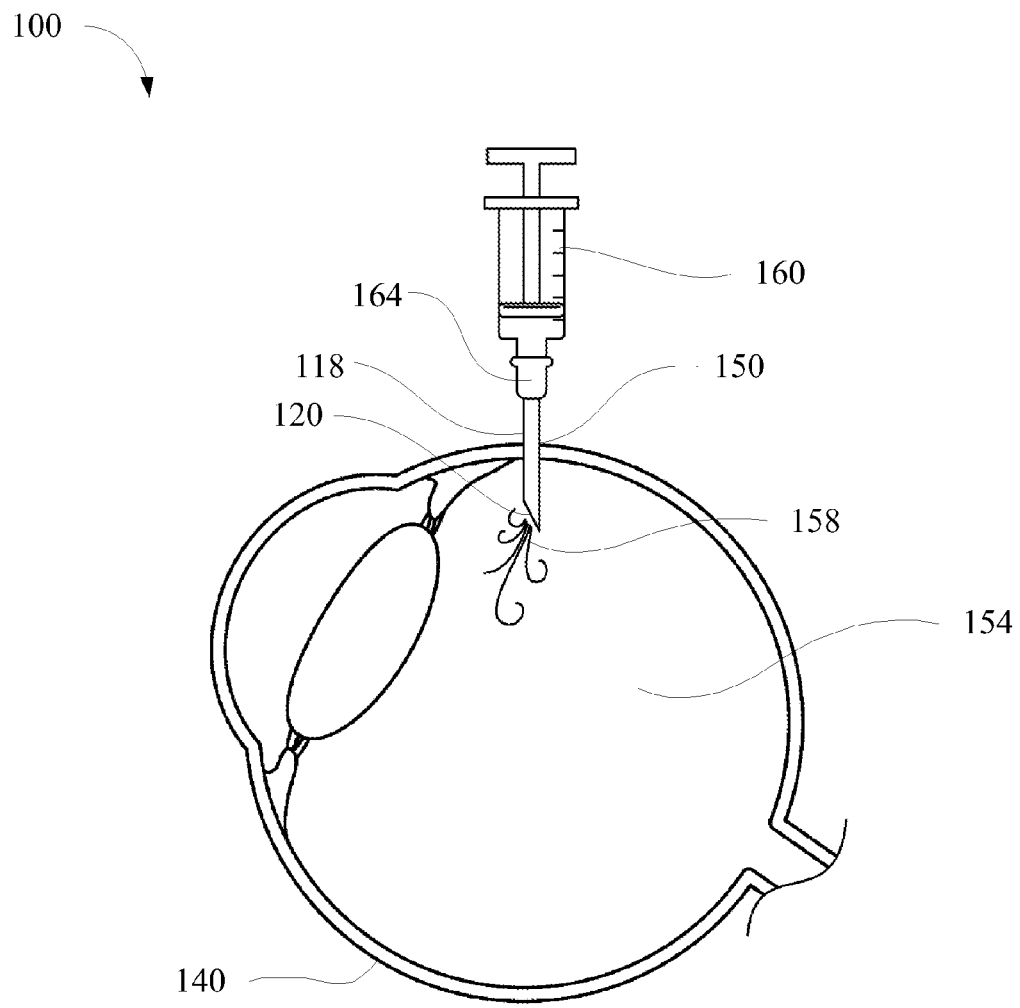
FIG. 3 shows a side, cross-section of an eye being injected with fluid according to principles of the present invention.

Turning now to FIG. 3, there is shown a side, cross-section of an eye 140 being injected with fluid 158, which is generally indicated at 100. The transmission of bacteria, fungi, and/or other contaminates into the inner eye may be reduced substantially by disposing an insert within the hollow channel 120 of the hypodermic needle 18 prior to penetration according to principles of the present invention. As explained above, the exterior surface of the hypodermic needle 118 tends to be wiped clean by structures between the outer membrane 150 and the intraocular space 154 of the eye 140. Thus, exposure of bacteria, fungi, and/or other infectious agents to the exterior surface of the needle 118 is of less concern than exposure of the same organisms to the inner surface of the needle 118. According to one aspect of the invention, once the hypodermic needle 118 is correctly positioned, the insert can then be removed from the hypodermic needle 118 and a medicament container 160, such as a syringe, may be attached and the drug delivered. Alternatively, as explained in more detail below, the insert may be removed while the needle 118 is attached to the medicament container 160 to minimize the risk of contaminating attachment member 164 when attaching medicament container 160. Thus it is believed that in a relatively simple manner the risk of infection due to injections in the eye 140 can be substantially reduced.

Figure 4:
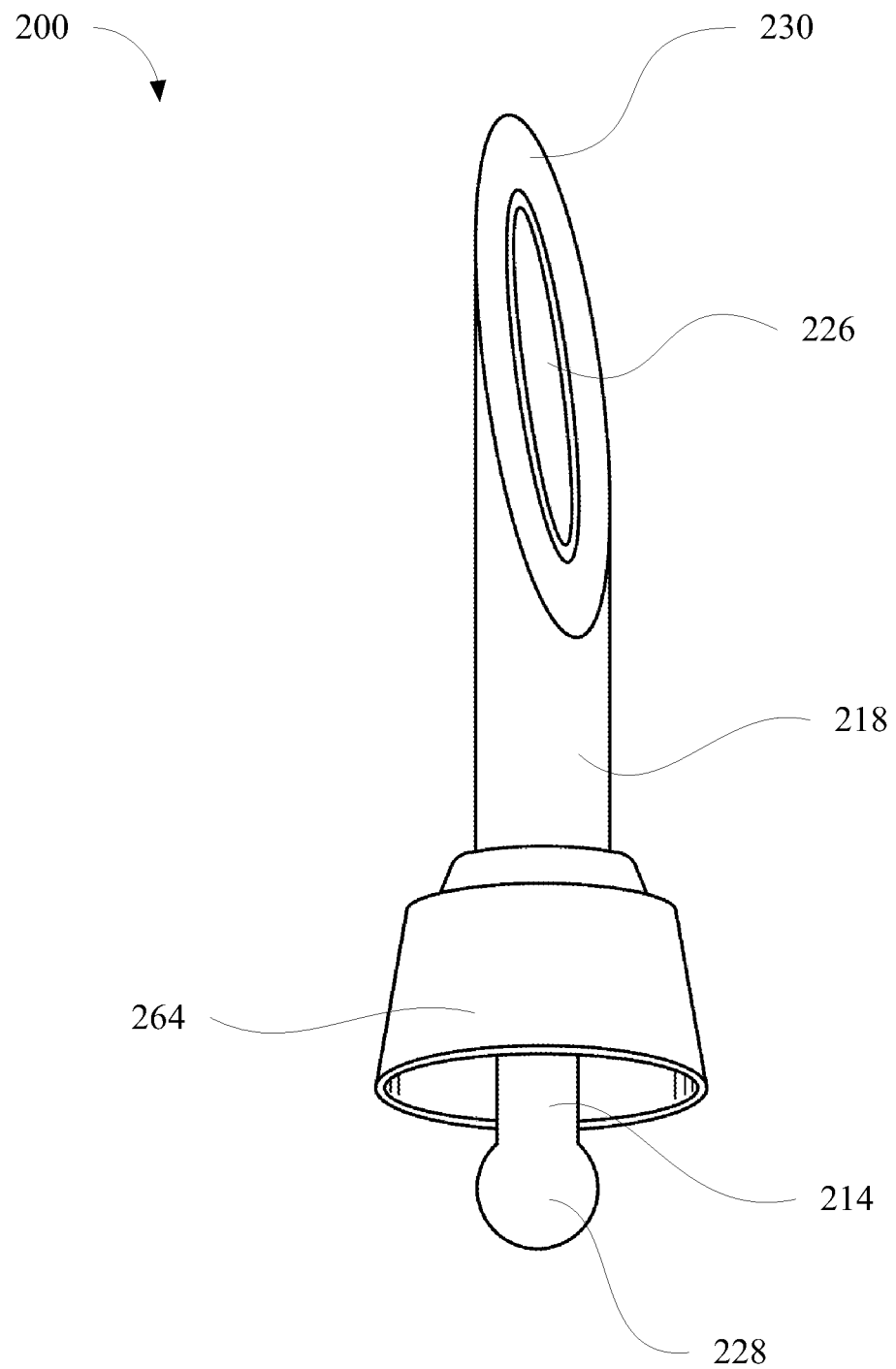
FIG. 4 shows a perspective view of a hypodermic needle system with an insert disposed in the hollow channel of a needle.

Turning now to FIG. 4, there is shown a perspective view of a hypodermic needle system, generally indicated at 200, with an insert 214 disposed in the hollow channel of a needle 218. The insert 214 may have beveled face 226 disposed in alignment with the beveled edge 230 of the needle 218 so as to form a substantially single, planar surface. At an opposite end of the insert 214 is a gripping member, such as knob 228. The gripping member 228 may be used to facilitate gripping the insert 214 in order to remove the insert 214 from the hollow channel after the needle 218 penetrates the exterior tissue surface. A user of the hypodermic needle system 228 may grip and twist the gripping member in order to initiate movement of the insert 214 within the hollow channel. It should be appreciated that a large variety of structures may be attached to the end of insert 214 to improve the ability of a user to grip the insert 214, such as a loop, hook, etc.

Once insert 214 is removed from the needle 218, a medicament container may be attached to the needle 218 via the attachment member 264 to thereby introduce the desired fluid to a human or animal via the now unobstructed hollow channel of needle 218. This may include a Luer lock attachment or any other suitable mechanism for connecting the syringe to the needle.

Figure 5:
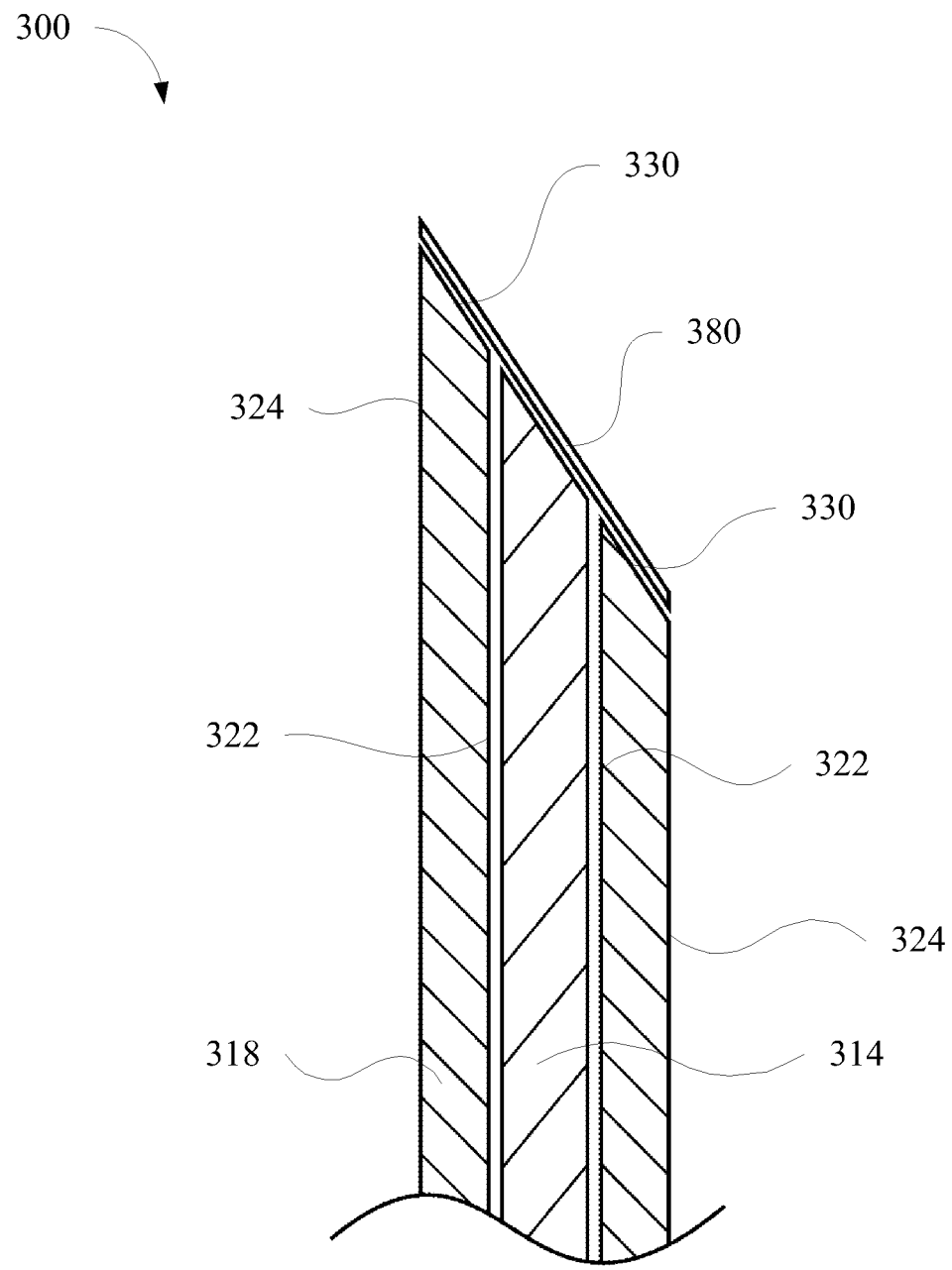
FIG. 5 shows a fragmented, cross-sectional side view of a hypodermic needle system of the present invention with a film covering the penetrating end of the hypodermic needle system.

Turning now to FIG. 5, there is shown a fragmented, cross-sectional side view of a hypodermic needle system, generally indicated at 300. A film 380 may cover the penetrating end of the hypodermic needle system 300. The film 380 may be comprised of a thermoplastic, such as poly methyl methacrylate (PMMA), cyanoacrylate compounds, or any other suitable material to which infectious agents have a reduced ability to adhere as compared to the surface of needle 318. Such a film may aid in the mechanical removal of bacteria and/or other infectious agents as the needle 318 passes through the outer layers of tissue being penetrated and fill in any gap where infective agents may be trapped and later injected into the eye. The film 380 may be attached to the insert 314 so that it may be removed and discarded with the insert 314 after the needle 318 has penetrated through the exterior tissue surface or may be removed where attached to the insert and remain where it is attached to the needle.

As shown in FIG. 5, the film 380 may extend over beveled edge 330 as well as the beveled face of insert 314. It should be appreciated that the surface area of needle 318 that is covered by film 380 is only representative and that hypodermic needle systems 300 according to principles of the present invention may have a film 380 that covers more or less of the exterior surface area of needle 318. For example, film 380 may extend past the beveled area of needle 318 to cover the exterior sidewalls 324.

Also an anti-infective agent (not shown) may be applied to the hypodermic needle system 300 in order to aid in reducing infections caused by procedures requiring injections. The anti-infective agent may be applied in addition to, as part of, or as an alternative to the film 380.

Figure 6:
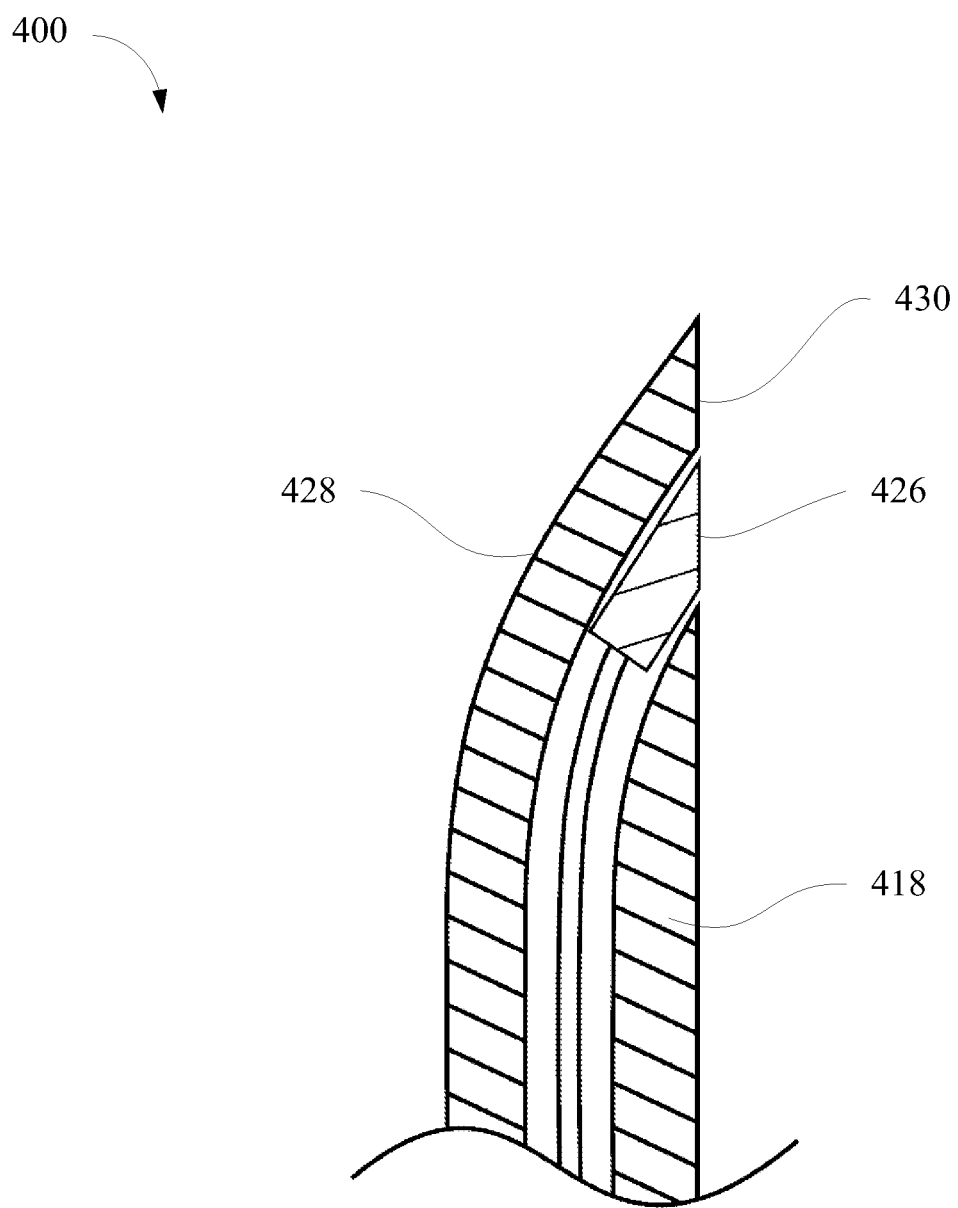
FIG. 6 shows a fragmented, cross-sectional side view of a hypodermic needle system of the present invention with a bent tip.

Turning now to FIG. 6, there is shown a fragmented, cross-sectional side view of a hypodermic needle system, generally indicated at 400, of the present invention with a bent or curved tip 428. Similar to the hypodermic needle systems described above, hypodermic needle system 400 may have an insert with a beveled face 426 disposed in alignment with the beveled edge 430 of the needle 418 so as to form a substantially single, planar surface. The tip of the needle 428, however, may be bent or curved at the bevel so that when the needle is advanced into a tissue, such as the conjunctiva, a linear puncture wound results. By providing hypodermic needle system 400 with bent tip 428 several known complications with intravitreal injections may be minimized or eliminated, such as incision gaping, vitreous prolapse, vitreous bulge, and/or vitreous wick.

Figure 7:
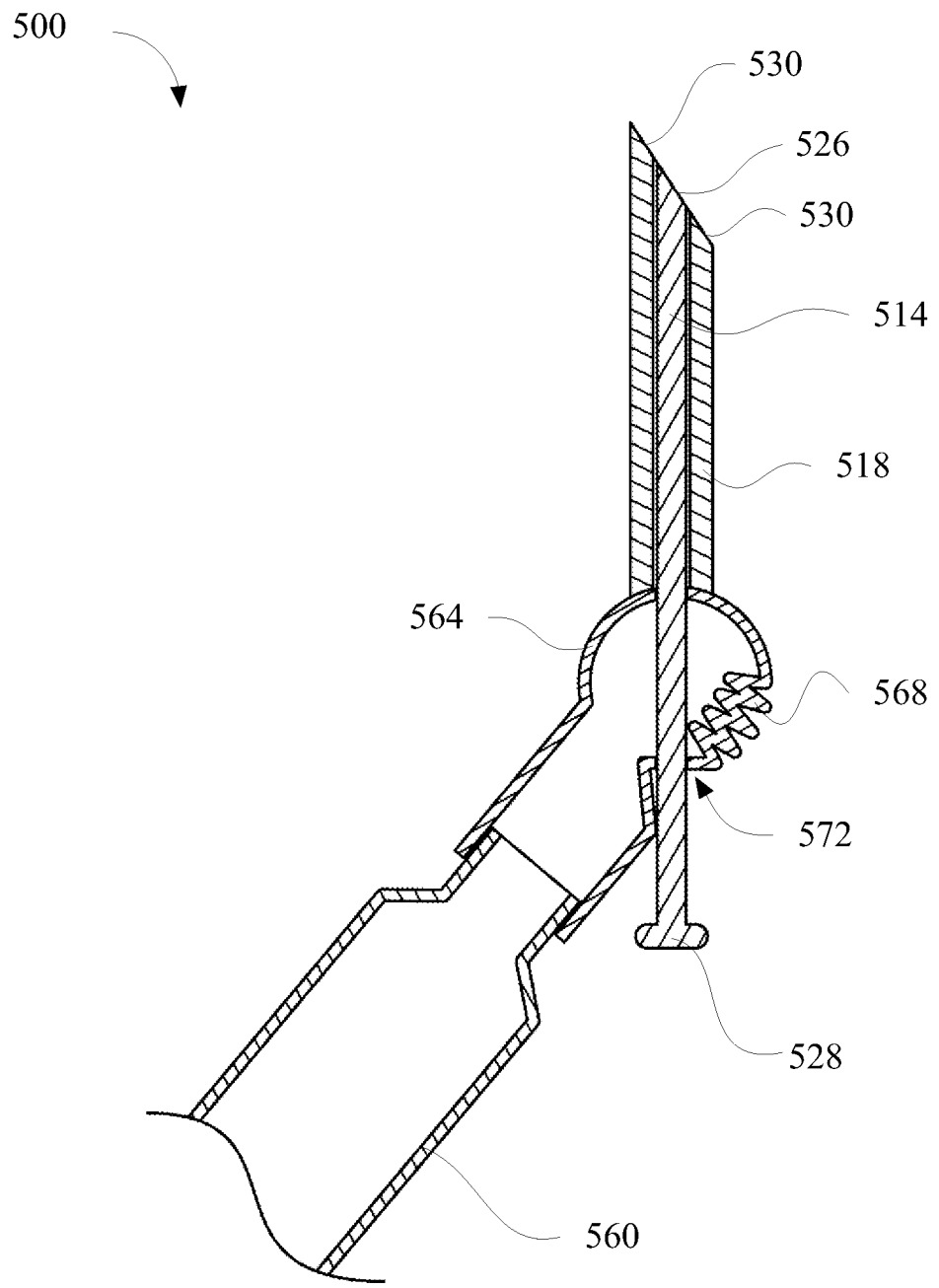
FIG. 7 shows a fragmented, cross-sectional side view of a hypodermic needle system with an insert extending from the hollow channel of a needle and through an opening in an attachment member of the needle.
Figure 8:
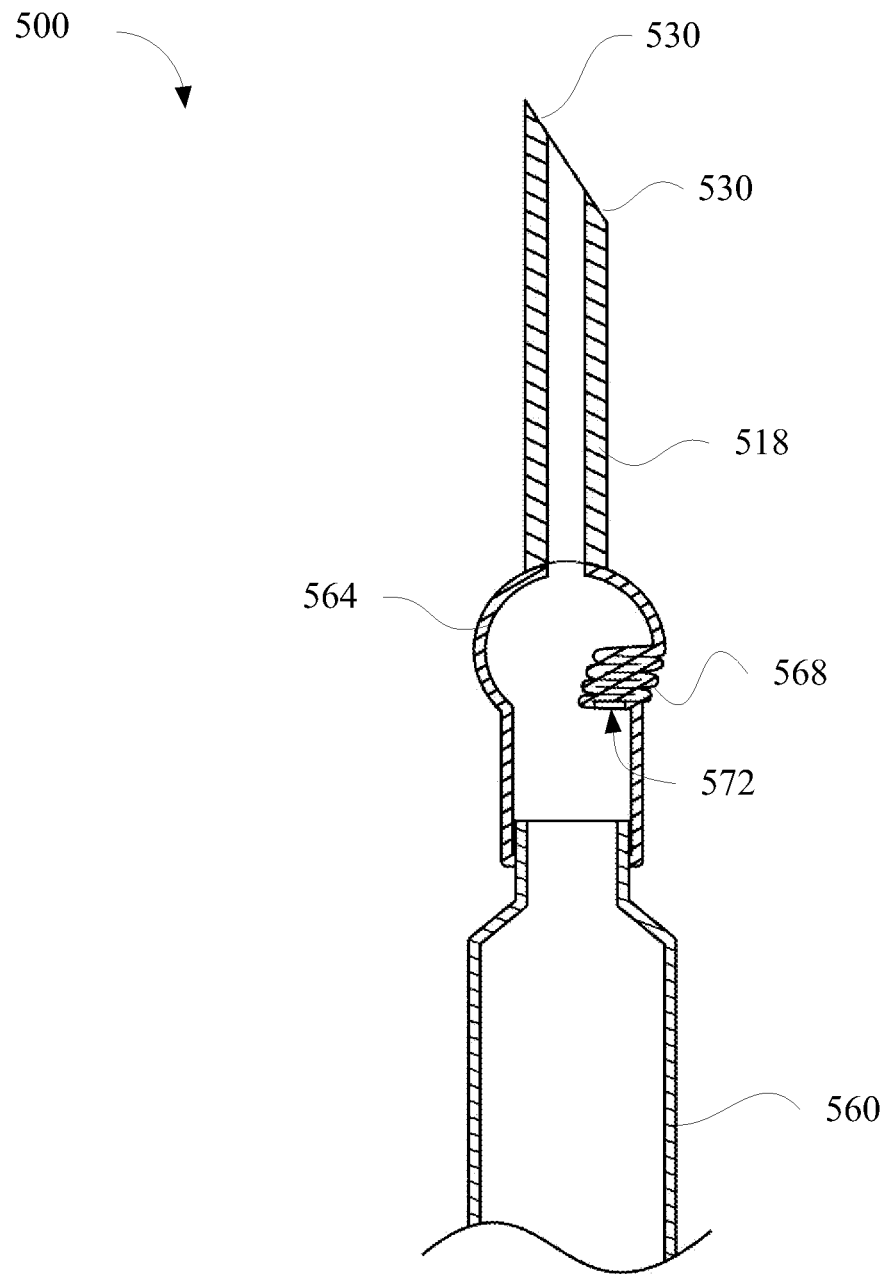
FIG. 8 shows a fragmented, cross-sectional side view of the hypodermic needle system of FIG. 7 with the insert removed.

Turning to FIG. 7, there is shown a fragmented, cross-sectional side view of a hypodermic needle system, generally indicated at 500, which may have an insert 514 extending from the hollow channel of a needle 518 and through an opening 572 in an attachment member 564 of the needle 518. A medicament container 560, such as a syringe, may be attached to attachment member 564 prior to using the needle 518 to penetrate an exterior tissue surface. Following penetration of an exterior surface by needle 518, the insert 514 may be removed through an opening 572. The attachment member 564 may have a movable section 568, such as a collapsible corrugated wall, which allows the medicament container 560 to be moved into substantially linear alignment with the needle 518. As shown in FIG. 8, when collapsed, the movable section 568 may be configured to substantially block opening 572. Thus, a fluid, such as a pharmaceutical compound or other therapeutic agent, in medicament container 560 may then be administered without fluid leaking from opening 572.

Figure 9:
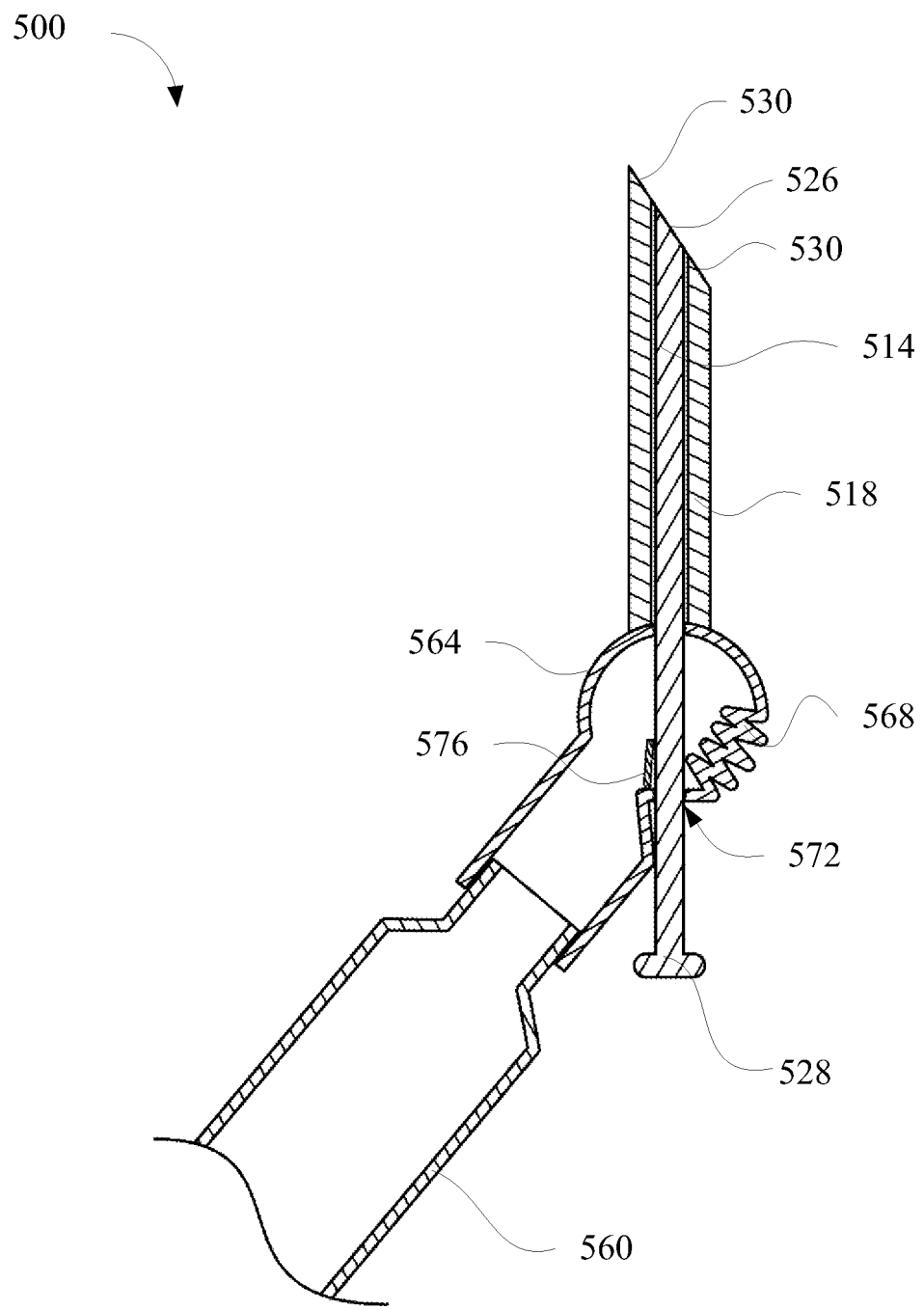
FIG. 9 shows a fragmented, cross-sectional side view of a hypodermic needle system with a flap for covering the opening in a corrugated attachment member after the insert is removed.
Figure 10:
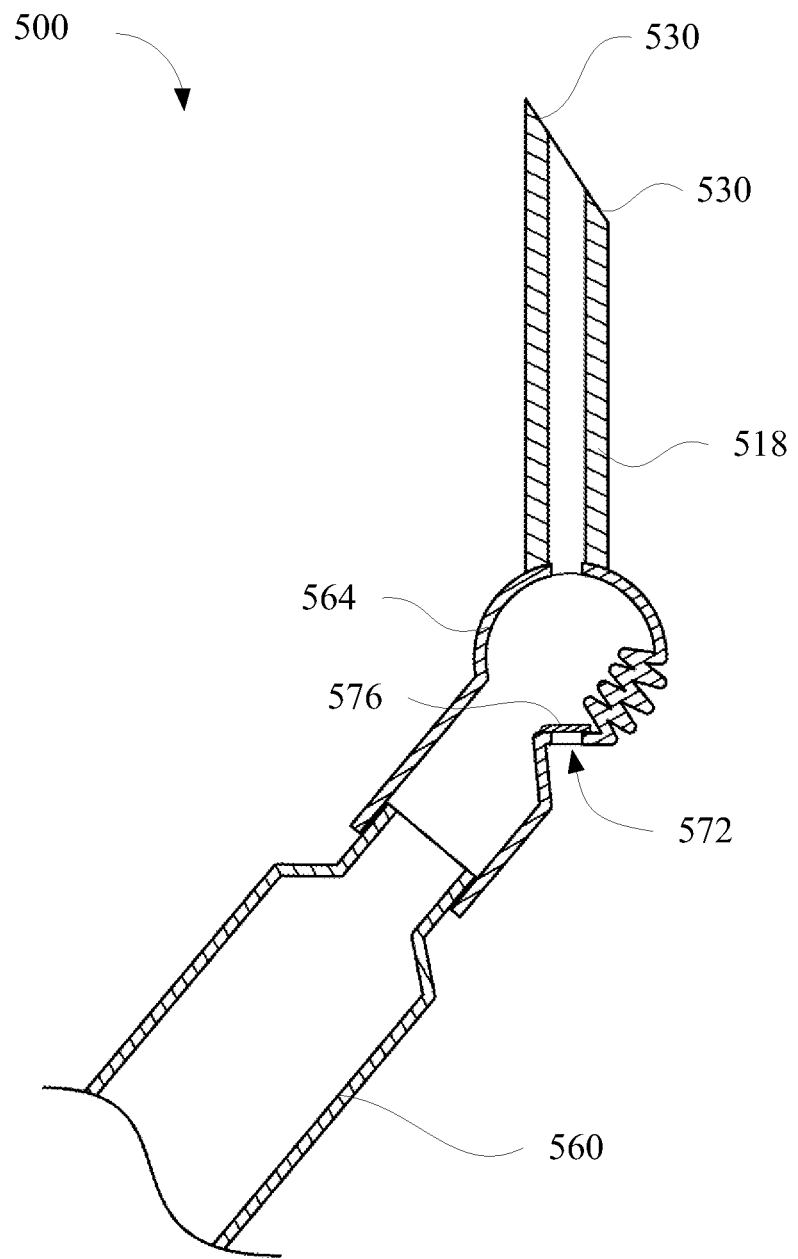
FIG. 10 shows a fragmented, cross-sectional side view of the hypodermic needle system of FIG. 9 with the flap over the opening in the corrugated attachment member after the insert is removed.

Attaching the medicament container 560 to attachment member 564 prior to using the needle 518 to penetrate an exterior tissue surface may increase the ease of use of hypodermic needle system 500. For example, it may be more difficult for medical personnel to attach the medicament container while the needle is in a patient. Moreover, attaching the medicament container 560 to attachment member 564 prior to using the needle 518 to penetrate an exterior tissue surface may minimize the risk of contaminating attachment member 564. FIGS. 9 and 10, show a cross-sectional, side view of another aspect of a hypodermic needle system 500, according to principles of the present invention. The hypodermic needle system 500 may include a flap 576 that is biased so that it closes over opening 572 after the insert 514 is removed therefrom. A wall 568, such as a corrugated or moveable wall, may then be collapsed or rotated, allowing the medicament container 560 to be moved into a substantially linear position with respect to the needle 518, as can be seen in FIG. 10. Flap 576 may better ensure that fluid does not leak through opening 572 when the fluid is administered to a patient using hypodermic needle system 500.

It will be appreciated that flap 576 may be moved to close opening 572 in a variety of ways. For example, hypodermic needle system may include an actuator to move flap 576 over opening 572 after the insert 514 is removed. Alternatively, hypodermic needle system 500 may include a biasing member that automatically moves flap 576 over opening 572 when insert 514 is removed.

It will also be appreciated that the moveable section 564 which allows the medicament container 560 to be moved into a substantial linear alignment with the needle 518 may include structures other than a corrugated wall, such as a slidable wall, etc. Furthermore, use of an actuator or some other method to move flap 576 over opening 572 may allow medical personnel to administer a pharmaceutical compound or other therapeutic agent without having to move the medicament container 560 into a substantial linear alignment with the needle 518.

There is thus disclosed a hypodermic needle system and method that substantially minimizes infections caused by injections of fluids in humans and animals that is easy to use and relatively inexpensive and easy to manufacture.

What is claimed is:

1. A hypodermic needle system comprising:
    a needle having a tip and a hollow channel, the hollow channel being covered at the tip by a film disposed on the tip of the needle, the film comprising a material which is resistant to the adherence of bacteria; and
    a removable insert, the film being attached to the insert;
    wherein the insert is disposed in the hollow channel of said needle so as to substantially prevent a contaminate from entering the hollow channel when the needle is advanced through a surface.

2. The hypodermic needle system according to claim 1, wherein the insert further comprises a line attached to the insert.

3. The hypodermic needle system of claim 1, wherein withdrawing the insert withdraws the film attached to the insert leaving open the end of the hypodermic needle.

4. The hypodermic needle system of claim 3, wherein the film comprises poly-methyl-methacrylate or a cyanoacrylate compound.

5. The hypodermic needle system of claim 1, further comprising an anti-infective agent comprised of an antiseptic agent.

6. The hypodermic needle system of claim 1, wherein the tip of the needle is bent.

7. The hypodermic needle system of claim 1, further comprising an attachment member for attaching the needle to a medicament container, and wherein the insert extends from the hollow channel of the needle through an opening in the attachment member when the needle is attached to the medicament container.

8. The hypodermic needle system of claim 7, wherein the attachment member comprises a movable section for pivoting the medicament container relative to the needle.

9. The hypodermic needle system of 8, wherein movement of the medicament container relative to the needle after the insert is removed causes the movable section to substantially block the opening in the attachment member.

10. The hypodermic needle system of claim 8, wherein the movable section comprises a corrugated wall.

11. The hypodermic needle system of claim 7, wherein the attachment member further comprises a flap for covering the opening in the attachment member after the insert is removed.

12. A hypodermic needle system comprising:
    a needle having a tip and a hollow channel having a distal end; and
    an insert;
    a film formed from a material which is resistant to the adherence of bacteria being attached so as to cover the distal end of the hollow channel, the film being attached to the insert;
    wherein the insert is disposed in the hollow channel of said needle so as to substantially prevent a contaminate from entering the hollow channel when the needle is advanced through a surface; and
    wherein the needle comprises a beveled edge and the insert comprises a beveled face and wherein the insert is disposed within the hollow channel such that the beveled edge of said needle and the beveled face of said insert are substantially aligned.

13. The hypodermic needle system according to claim 12 wherein the beveled edge of the needle and the beveled face of the insert substantially comprise a planar surface.

14. A method for reducing the risk of infection when injecting a human or animal, the method comprising:
    selecting a needle having a tip and a hollow channel and having an insert disposed within the hollow channel so as to substantially prevent a contaminant from entering the hollow channel, at least one of the tip of the needle and the insert having a material disposed thereon which is resistant to adherence of micro-organisms thereon, the material covering the hollow channel at the tip;

advancing the needle into a tissue;

removing the insert and material disposed thereon from the needle after advancing the needle into the tissue; and administering a fluid through said hollow channel and into the human or animal.

15. The method for reducing the risk of infection according to claim 14, wherein the insert further comprises a line attached thereto.

16. The method for reducing the risk of infection according to claim 14, wherein the insert further comprises a gripping member for facilitating removal of the insert from the hollow channel.

17. The method for reducing the risk of infection according to claim 14, wherein the material comprises a film disposed on at least one surface of the needle or insert prior to advancing the needle into the tissue to substantially eliminate any space where micro-organisms might be trapped.

18. The method for reducing the risk of infection according to claim 17, wherein the film is attached to the insert and wherein the method comprises removing the insert so as to remove the film covering the hollow channel at the tip of the needle.

19. The method for reducing the risk of infection according to claim 14, wherein the method further comprises the step of applying an anti-infective agent to at least one surface of the needle or insert prior to advancing the needle into the tissue.

20. The method for reducing the risk of infection according to claim 14, wherein the material is a film attached to the insert prior to advancing the needle into the tissue, wherein the film comprises an anti-infective agent.

21. The method for reducing the risk of infection according to claim 14, wherein the tip of the needle is bent so that advancing the needle into the tissue results in a substantially linear puncture wound.

22. The method for reducing the risk of infection according to claim 14, wherein the method further comprises the step of attaching the needle to a medicament container via an attachment member prior to advancing the needle into a tissue, and wherein the attachment member includes an opening through which the insert extends.

23. The method for reducing the risk of infection according to claim 22, wherein the method further comprises the step of moving the medicament container relative to the needle about a movable section of the attachment member.

24. The method for reducing the risk of infection according to claim 23, wherein movement of the medicament container relative to the needle causes at least a portion of the movable section to substantially block the opening in the attachment member after the insert is removed.

25. The method for reducing the risk of infection according to claim 22, further comprising the step of covering the opening in the attachment member with a flap after the insert is removed.

* * * * *